United States Patent
Beaton et al.

(10) Patent No.: US 10,339,271 B2
(45) Date of Patent: Jul. 2, 2019

(54) INTELLIGENT ELIGIBILITY REQUEST AND RESPONSE

(71) Applicant: Passport Health Communications, Inc., Franklin, TN (US)

(72) Inventors: Stuart L. Beaton, Brentwood, TN (US); Donavon R. Feenstra, Cane Ridge, TN (US)

(73) Assignee: PASSPORT HEALTH COMMUNICATIONS, INC., Franklin, TN (US)

( * ) Notice: Subject to any disclaimer, the term of this patent is extended or adjusted under 35 U.S.C. 154(b) by 219 days.

(21) Appl. No.: 14/046,851

(22) Filed: Oct. 4, 2013

(65) Prior Publication Data

US 2014/0100865 A1 Apr. 10, 2014

Related U.S. Application Data

(60) Provisional application No. 61/710,385, filed on Oct. 5, 2012.

(51) Int. Cl.
*G06F 19/00* (2018.01)
*G06Q 10/10* (2012.01)

(52) U.S. Cl.
CPC ........... *G06F 19/328* (2013.01); *G06Q 10/10* (2013.01)

(58) Field of Classification Search
USPC ........................................................ 705/2–4
See application file for complete search history.

(56) References Cited

U.S. PATENT DOCUMENTS

| 6,175,869 | B1* | 1/2001 | Ahuja | H04L 67/1008 709/203 |
| 6,965,777 | B1* | 11/2005 | Cast | H04L 51/38 370/237 |
| 8,667,056 | B1* | 3/2014 | Proulx | H04L 67/325 370/229 |
| 8,762,181 | B1* | 6/2014 | Ringold | 705/4 |
| 8,781,850 | B2* | 7/2014 | Bazzani et al. | 705/2 |
| 2003/0078911 | A1* | 4/2003 | Haskell et al. | 707/2 |

(Continued)

OTHER PUBLICATIONS

"Quick Guide to Eligibility Transaction Service Type Codes" as presented by Aetna (available at www.aetna.com/provider/data/5010_41747.pdf as published online on Oct. 6, 2010).*

(Continued)

*Primary Examiner* — Mark Holcomb
(74) *Attorney, Agent, or Firm* — Merchant & Gould

(57) ABSTRACT

Eligibility benefit information associated with a subscriber or dependent may be requested by a provider in an eligibility request, for example, a 270 request. Embodiments may intelligently determine a most appropriate service type code (STC) for a provider's eligibility request based on their location ("where") and on the provider type ("who"). Utilizing precision STC tables for a payer ("what") and the identity of the "who" and "where" associated with the provider sending the request, appropriate component level (and if needed, explicit level) STCs may be submitted in an intelligent eligibility request. Accordingly, an appropriately detailed yet focused response to the request may be received.

20 Claims, 4 Drawing Sheets

(56) References Cited

U.S. PATENT DOCUMENTS

| | | | |
|---|---|---|---|
| 2003/0156547 A1* | 8/2003 | Peleg | H04L 29/06 370/252 |
| 2003/0171953 A1* | 9/2003 | Narayanan et al. | 705/2 |
| 2006/0149603 A1* | 7/2006 | Patterson et al. | 705/4 |
| 2009/0157435 A1* | 6/2009 | Seib | 705/4 |

OTHER PUBLICATIONS

"Louisiana Medicaid Management Information Systems Vendor Specifications Document for the Medicaid Eligibility Verification System", Version 1.5, May 28, 2007, hereinafter MEVS, available at http://www.lamedicaid.com/provweb1/HIPAAbilling/EDI_VSD_LA_MEVS_NPI_5-28-2007%20ver1_5.pdf.*

"Highmark West Virginia Standard Companion Guide", Version 1.0, Feb. 2011 (available at https://www.highmark.com/edi-wv/pdfs/5010providerguide.pdf).*

"HIPAA Eligibility Transaction System (HETS) Health Care Eligibility Benefit Inquiry and Response (270/271) Companion Guide", Centers for Medicare & Medicaid Services, Dec. 20, 2011, available at file:///C:/Users/mholcomb/Documents/e-Red%20Folder/14046851/HETS-270-271-Companion-Guide%20NPL.pdf.*

"CMS Manual System", Dep. Health and Human Services, Jan. 15, 2010, available at file:///C:/Users/mholcomb/Documents/e-Red%20Folder/14046851/R623OTN%20NPL.pdf.*

"Additional Information Message Implementation Guide", Health Level Seven, Inc., Dec. 11, 2001, available at file:///C:/Users/mholcomb/Documents/e-Red%20Folder/14046851/HL7CImAttIG%20NPL.PDF.*

"Emdeon Office: Real Time User Guide" (Feb. 2012, available at https://office.emdeon.com/HOME/user_guide_real-time.pdf).*

* cited by examiner

INTELLIGENT ELIGIBILITY REQUEST AND RESPONSE

CROSS-REFERENCE TO RELATED APPLICATIONS

The application claims priority to U.S. Provisional Patent Application No. 61/710,385 titled "3D Eligibility Request and Response" filed Oct. 5, 2012, the disclosure of which is hereby incorporated by reference in its entirety.

BACKGROUND

When a patient seeks healthcare services from a healthcare provider, the provider may request information from a payer (e.g., insurance company) to determine if the patient is eligible to receive benefits for healthcare services; and if the patient is eligible, other benefit and eligibility information such as benefit amounts, co-insurance, co-pays, deductibles, exclusions, and limitations related to a specific procedure may be provided. The request for information may be sent as an eligibility request, for example, a 270 request or transaction. A payer may communicate eligibility benefit information associated with a subscriber or dependent in a response, for example, a 271 response or reply.

The eligibility request and response may be required to meet transaction processing standards. For example, eligibility transactions may be sent in an X12 syntax format and may be coded and structured according to standards established by the Secretary of Health and Human Services (HHS) as required by the Health Insurance Portability and Accountability Act of 1996 (HIPAA). As is known in the art, HIPAA includes provisions for administrative simplification and support electronic exchange of administrative and financial healthcare transactions primarily between healthcare providers and plans. As should be appreciated, embodiments may be utilized with other formats, structures, and syntaxes according to changes in healthcare laws. For example, a 270 eligibility request may be replaced by an eligibility request of another format and utilizing an alternate syntax. A 271 response may be replaced by an eligibility response of another format and utilizing an alternate syntax.

Prior to Jan. 1, 2012, the transaction standard in use was the X12 version 4010A1. The 4010 transaction standards drove billing, reimbursement, and administrative functions. As is known in the art, the 4010 standards provided a one-size-fits-all type of eligibility response driven by a service type code (STC) 30 (Health Benefit Plan Coverage) in the 270 eligibility request. For example, payers would sometimes return a large list of service type codes (i.e., benefits) that were covered in a patient's health plan, and sometimes even service type codes that were not covered. In addition, some payers would include a patient's portion of financial responsibility (e.g., co-payment, deductible amount, co-insurance, etc.) at the plan and sometimes at the benefit level. A challenge to providers receiving this type of response was sifting through the large amount of data returned by the payer to locate the benefits that were relevant to the provider and their patient. The challenge was sometimes compounded by some payers returning free form text forcing human interpretation rather than a systematic approach to reviewing a response.

To help provide improvements to electronic data interchange (EDI) transactions including greater clarity in provider loops and national provider identifier (NPI) instructions, reduced ambiguity among common data elements, and elimination of unnecessary or redundant data elements, the 5010 transaction standard was developed. Therefore, HIPAA X12 version 5010 became the new set of standards regulating the electronic transmission of specific health care transactions including eligibility, claim status, referrals, claims, and remittances.

A first phase of operating rules requirements for the 5010 version of the 270/271 transaction was adopted, the 5010 version outlining a set of benefit groupings based on ten high level category service type codes that payers can support. For example, a hospital may send a 270 request with an STC 47 (i.e., service type code for a hospital); and accordingly, the payer would reply with relevant benefits for a hospital and suppress benefits only relating to the other nine high level service type codes. This is referred to as a component level request and response.

Subsequently, a second phase of operating rules was adopted, adding an additional thirty-six STCs to which payers would have to respond. This is referred to as an explicit STC request and response. The explicit STC request and response is more focused than the component level request and response.

As payers moved from the 4010 standards to the 5010 standards for the 270/271, many of them adopted the support for the component level request and response and thus removed many of the details that were sent in a 4010 generic response. The details were returned when a component level request or an explicit STC request was received.

As providers migrated from 4010 to 5010 and the payers they processed eligibility transactions with also migrated from 4010 to 5010, providers saw the level of details change in their responses to a generic STC 30 inquiry. For some health plans, a greater amount of details came back, particularly for payers that sent a bare minimum 4010 response. For other payers, less detail was provided in the generic response as those details were moved to either a component level response or an explicit STC response.

Many providers may not be aware of the component level or explicit STC request and response capabilities that the payers implemented, and merely perceived this as a reduction in the level of information that was being returned. Additionally, many Health Information System vendors only allow for the submission of a STC 30. The result has been that those providers may see a lot less information in their 271 eligibility responses. In some cases, this may result in a perceived degradation of service (even if the missing information was irrelevant to them); however, in some cases, some detail in the mountain of data returned in a generic STC 30 response had value to the provider. The trend will likely continue as payers implement the ACA Operating Rules which require them to offer component and explicit service type code requests.

It is with respect to this and other considerations the present invention has been made.

SUMMARY

Embodiments of the present invention provide for creating an intelligent 270 request comprising component and/or explicit service type codes. By identifying the provider of the 270 request ("who"), the health plan the transaction is being sent to and the responses capabilities they have depending on the service type code sent ("what"), and in some cases the department or location the 270 request is coming from ("where"), an intelligent 270 request comprising component or explicit service type codes (or combinations) may be created. Embodiments provide for creating such requests and for providing accessibility through a self service portal. Embodiments require little or no effort on the provider's part and provide an appropriate response for provider customers.

DETAILED DESCRIPTION

Figure 1:
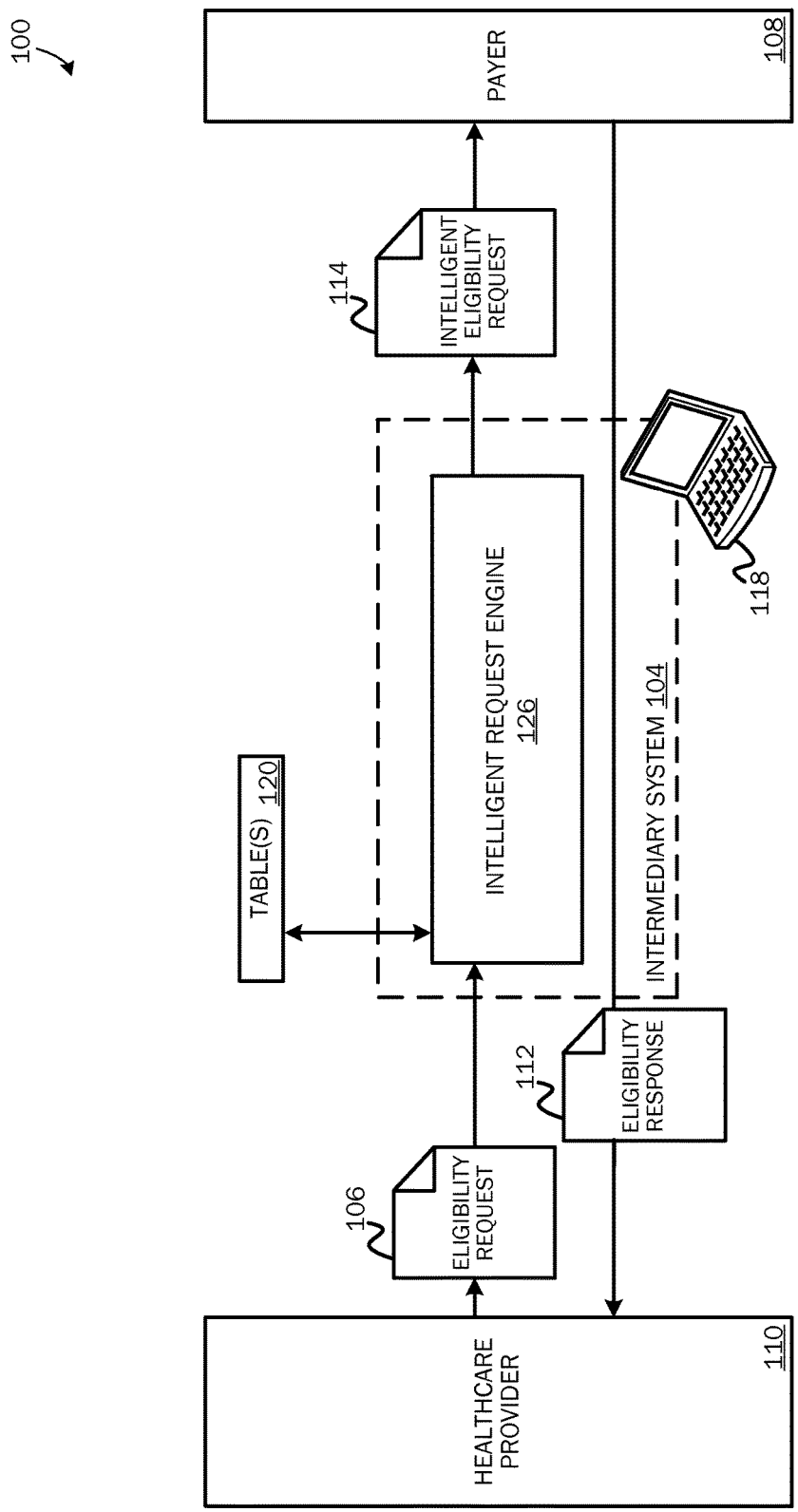
FIG. 1 is a simplified block diagram of a high-level system architecture with which embodiments of the invention may be implemented.

Embodiments provide for creating an intelligent eligibility request comprising component and/or explicit service type codes. As briefly described above, eligibility benefit information may be transmitted between payers and the healthcare provider community in a standard format according to healthcare laws, for example, HIPAA. Eligibility benefit information associated with a subscriber or dependent may be requested by a provider in an eligibility request, for example, a 270 request. Embodiments may intelligently determine a most appropriate service type code (STC) for a provider's eligibility request based on a payer's location ("where") and on the provider type ("who"). Utilizing precision STC tables for a payer ("what") and the identity of the "who" and "where" associated with the provider sending the request, appropriate component level (and if needed, explicit level) STCs may be submitted in an intelligent eligibility request. Accordingly, an appropriately detailed yet focused response to the request may be received. The eligibility response may be received by the sender, which may be the intermediary system or a healthcare provider.

According to embodiments, embodiments may comprise an intelligent request engine operable to determine a "who" dimension of the eligibility request. That is, the intelligent request engine may be operable to determine from whom (i.e., provider) and to whom (i.e., payer) an eligibility request is being sent. Additionally, the intelligent request engine may be operable to determine a department and/or facility type from where the eligibility request is being sent. For example, due to a variety of reasons, a generic eligibility request may be sent by a provider that does not specifically ask for an emergency services based response. Additional data in the eligibility request may be parsed for attributes that may indicate a specific department type which may be utilized to create an intelligent eligibility request.

According to embodiments, the intelligent request engine may be operable to determine a "where" dimension of an eligibility request. That is, the intelligent request engine may be operable to determine who may ultimately respond to the request and where they are located.

According to embodiments, the intelligent request engine may be operable to determine a "what" dimension of the eligibility request. That is, the intelligent request engine may be operable to determine what information the provider may want to receive in an eligibility response (i.e., response STCs) and what STCs to include in an intelligent eligibility request to prompt the desired response STCs. The determination may be based on one or more service type codes (STCs) provided by the provider. According to an embodiment, other attribute data may be utilized to determine ideal response STCs and what STCs to include in the intelligent eligibility request.

These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents. Referring now to the drawings, in which like numerals refer to like elements throughout the several figures, embodiments of the present invention and an exemplary operating environment will be described.

Referring now to FIG. 1, a simplified block diagram of a high-level system architecture 100 with which embodiments of the invention may be implemented is illustrated. The system 100 may include an information requester (referred to herein as a healthcare provider 110). The healthcare provider 110 may request information about healthcare coverage eligibility and benefits associated with a health plan subscriber or dependent of a health plan subscriber. The request for information may be in the form of an eligibility, coverage, or benefit inquiry (herein referred to as an eligibility request 106). The eligibility request 106 may be sent directly to a responder (referred to herein as a payer 108) or alternatively, may be sent to a payer 108 via an intermediary system 104. Because there are many different ways to communicate with various entities in a healthcare system, an intermediary system 104 may be utilized to normalize communication solutions, data requirements, and transaction formats for their business partners.

According to embodiments, the system 100 may comprise an intelligent request engine 126. In the illustrated embodiment, the intelligent request engine 126 is executed on a computing device 118. An eligibility request 106 may be restructured into an intelligent eligibility request 114 by the intelligent request engine 126 or an intelligent eligibility request 114 may be created by the intelligent request engine 126. Although the intelligent request engine 126 is illustrated as located at the intermediary system 104, the intelligent request engine 126 may be implemented within a healthcare provider system 110 or may be located remotely and accessed via a network. The intelligent request engine 126 may be implemented using one or more computing devices 118. The intelligent request engine 126 may be operable to receive an eligibility request 106 or eligibility request data. According to an embodiment, the system 100 may comprise an in-process scripting (IPS) product that may be operable to capture information from a screen generating the eligibility request 106.

The system 100 may include a plurality of tables 120 which may be utilized to identify the "who," "when," and "what" associated with an eligibility request 106 and to determine what STCs to include in the intelligent eligibility request 114 based on the "who," "when," and "what." For example, the tables 120 may include a hospital service type code (HPSTC) to X12 STC mapping table, an intelligent request STC to ideal response STC mapping table, a home plan code prefix lookup table, and a payer X12 STC response table.

The intelligent request engine 126 may be operable to receive an eligibility request 106 or eligibility request data, determine attributes associated with the request 106, and create an intelligent eligibility request 114 using component and/or explicit service type codes. The attributes may comprise one or more of: a client ID, a destination data source line of business pathway version ID number (DLPVID), a transaction reference number, a member ID, an X12 STC or a hospital proprietary STC (HPSTC). Other attributes may comprise: a request source, a trading partner ID, a user ID, a department type, other hospital information system (HIS) standard (e.g., HL7) data (e.g., patient class, assigned patient location, admission type, admit source, patient type, etc.), other X12 data (e.g., placed of service, provider role, etc.), etc. According to an embodiment, if multiple STCs are received, a determination may be made as to whether multiple X12 STCs will be supported in the intelligent eligibility request object.

If a received STC is a HPSTC, the intelligent request engine 126 may be operable to query a table 120 and convert the HPSTC to an X12 STC. According to embodiments, the system 100 may include a plurality of tables 120 which may be utilized to identify the "who," "when," and "what" associated with an eligibility request 106 and to determine what STCs to include in the intelligent eligibility request 114 based on the "who," "when," and "what." For example, the tables 120 may include a hospital service type code (HPSTC) to X12 STC mapping table, an intelligent request STC to ideal response STC mapping table, a home plan code prefix lookup table, and a payer X12 STC response table.

The HPSTC to X12 STC mapping table may be utilized to map a provider's 110 proprietary hospital proprietary service type codes to X12 service type codes. As should be appreciated, although described as X12 STCs, embodiments may include a variety of transaction standard formats and is not limited to X12 STCs. The following table is an example of an HPSTC to X12 STC mapping table:

| HPSTC to X12 STC Table Example | | |
| --- | --- | --- |
| Hospital Service Code | Service Type | X12 Service Type Code |
| ANS | Surgical | 2 |
| BMT | Transplants | 70 |
| LT1 | Long Term Care | 54 |
| LT2 | Long Term Care | 54 |
| MFM | Maternity | 69 |
| NB | Well Baby Care (Healthy Baby) | 68 |
| OMS | Rehabilitation | A9 |
| ONN | Neonatal Intensive Care | NI |

| Hospital Service Code | Bed Type | Service Type Code |
| --- | --- | --- |
| Te | Transitional Care | TC |
| Ac | Alcoholism | AJ |

If a received X12 STC is not an STC 30, various attributes may be utilized to determine an appropriate intelligent STC. Depending on the source of the request, the attributes may vary. Base attributes may comprise: a trading partner ID, client ID, user ID, and a department. Some or all of these attributes may be utilized to map to an intelligent STC. Other attributes may comprise: client user ID, user ID, admission source, admission type, facility type, and patient class.

If a received X12 STC is an STC 30, a table 120, for example the intelligent request STC to ideal response STC mapping table, may be queried to determine if the X12 STC is a code in an intelligent STC list. As described above, the system 100 may include an intelligent request STC to ideal response STC mapping table.

A list of STCs may be identified that represent a "who" and "where" entity. The list may be a normalized list to which the various attributes that are used to identify the "who" and "where" are mapped. For example, a hospital ("who") emergency department ("where") may be normalized to an intelligent request STC 86-Emergency Services. For each intelligent request STC, an ideal group of STCs that a provider 110 would want to receive as response data may be identified. For example, for the intelligent request STC 86—Emergency Services, a provider 110 may want to receive benefit and financial information relating to: 86—Emergency Services, 4—Diagnostic X-Ray, 5—Diagnostic Lab, 51—Hospital—Emergency Accident, 51—Hospital—Emergency Medical, 73—Diagnostic Medical, CK—Screening X-ray, CL—Screening laboratory, etc.

The intelligent request STC to ideal response STC mapping table may identify an intelligent request STC, a description of the STC, and a set of ideal benefits desired to be returned in an eligibility response 112 for the STC. The intelligent request STC to ideal response STC mapping table may be comprised of high level component (e.g., X12 5010 STC components) and other category STCs (Phase I and II Operating Rules) and ideal response STCs (i.e., common/expected STCs provided in a response 112) that should be returned for each intelligent request STC. Input from various patient access workflow engines may be utilized to create the intelligent request STC to ideal response STC mapping table The intelligent request STC to ideal response STC mapping table provides a broad set of benefit categories and identifies payer 108 by payer what STCs are needed to be sent to those payers 108 to return the needed information for that benefit category. For example, for an Emergency Room based inquiry, benefits associated with STCs 86 (Emergency Services), 51 (Hospital—Emergency Accident) and 52 (Hospital—Emergency Medical) may be desired. For each payer 108, embodiments would determine what STC code(s) would need to be sent to return these 3 STCs and their associated benefits as well as copayment, coinsurance, deductible or other financial responsibility amounts.

The following table is an example of an intelligent request STC to ideal response STC mapping table:

| | Example Intelligent Request STC to Ideal Response STC Mapping Table | | | | |
| --- | --- | --- | --- | --- | --- |
| | Benefit | | | | |
| Payer | Emergency Room (86, 51, 52) | Hospital - Inpatient (48, 49, 50, 5, 51, 53) | Radiology (4, CK) | CT/MRI Imaging (62, 4, 50, 73, 9, 96) | Inpatient Psychiatric (A7, A4, A5, MH) |
| Payer A | 86 | 47 | 4, CK | 62 | MH, A7 |
| Payer B | 86 | 47 | 4 | 62 | MH |
| Payer C | 30 | 30 | 30 | 30 | 30 |
| Payer D | 86, 47 | 47 | 4, CK | 62, 4, 50, 9, 96 | MH |

In addition to being able to set up a default benefit category for "who" and "where," embodiments also support focused high level benefit category requests, where a provider 110 may send in a single service type code and a corresponding intelligent eligibility request 114 may be generated for the payer 108. For example, if a provider 110 wanted Inpatient Psychiatric Benefits, they would submit A7 in their eligibility request 106, and using the intelligent request STC to ideal response STC mapping table, embodiments may be utilized to ensure that the correct STC(s) are sent to the payer 108 to generate a focused response 112. For any STC not in the intelligent request STC to ideal response STC mapping table, embodiments may pass through the value as received (for example if 2—Surgical was not in the table, it would be passed to the payer as a 2).

The intelligent eligibility request 114 may be formulated specific to the payer 108 that is ultimately responding to the request. Each payer's capabilities to respond to an X12 STC may vary. According to embodiments, the intelligent request engine 126 may be operable to determine who may ultimately respond to the request and where they are located.

For example, a patient may have insurance coverage provided by a payer 108 which may be part of an association of payers. The patient may have a health plan with a payer 108 of one state (e.g., California) and may seek healthcare services in another state (e.g., Tennessee). In such a case, if the association includes a payer 108 in the state where the patient is receiving healthcare services, an eligibility request 106 may be sent to that payer 108. Ultimately, the payer 108 may forward the request to the payer 108 with whom the patient's plan is a member. Although part of the same association, each payer 108 may respond to requests differently. According to an embodiment, the determination may be based on a destination data source line of business pathway version ID number (DLPVID). Data such as the patient's member identification number and prefix may also be used to determine the payer 108 and their location.

Each payer's 108 capabilities to respond to an X12 STC may vary. For example, some payers 108 may return many related STCs, while others may only return the same STC as received. A determination may be made as to what may be the least number of X12 STCs to send a payer 108 to receive the maximum number of the Ideal Response X12 STCs.

Various inquiry processing systems may have different time out limits. Accordingly, a determination may be made to determine the maximum number of STCs that should be sent in the list of payer X12 STCs without experiencing a time out issue trying to get too many of the ideal X12 STCs back from a payer 108. This may be based on items such as how many STCs the payer 108 can support in a single 270 request 106, average response time for the DLPVID, timeout by DLPVID, communication pathway (single socket, dual socket), etc.

According to an embodiment, only a maximum number of STCs (or a percentage of the maximum number of STCs) that will not cause a time out issue may be sent. For example, if the payer can only support 1 STC per 270 eligibility request 106, and they have an average response time of 6 seconds, and the product the provider is using has a time out of 60 seconds, the maximum number of STCs that may be included in an intelligent eligibility request 114 may be 10.

The system 100 may include a payer X12 STC response table. As described above, each payer 108 may respond differently to each STC they receive. Accordingly, the payer X12 STC response table may identify what data is returned by a payer 108 in eligibility responses 112 for each of the X12 STCs supported by the payer 108. Eligibility responses 112 may be monitored such that new STCs may be identified and added to the table and non-supported STCs may be removed from the table. Alerts may be provided when an expected code is no longer returned such that the payer X12 STC response table may be updated.

The following table is an example of a payer X12 STC response table:

Example Payer X12 STC Response Table

| DLPVID | PAYER | STC | STC Description | Response Type: Active | Response Type: Financial |
|---|---|---|---|---|---|
| 2790 | Ins A | 1 | Medical Care | 30^33^47^48^50 ^86^98^UC^35^A L^MH^88 | 30^33^48^50^86 98^UC |
| 2790 | Ins A | 2 | Surgical | 30^2 | 30^2 |
| 2790 | Ins A | 45 | Hospice | 30^45 | 30^45 |
| 2790 | Ins A | 65 | Newborn Care | 30^65 | 30^65 |
| 2790 | Ins A | 69 | Maternity | 69 (no 30) | None |

Figure 2A:
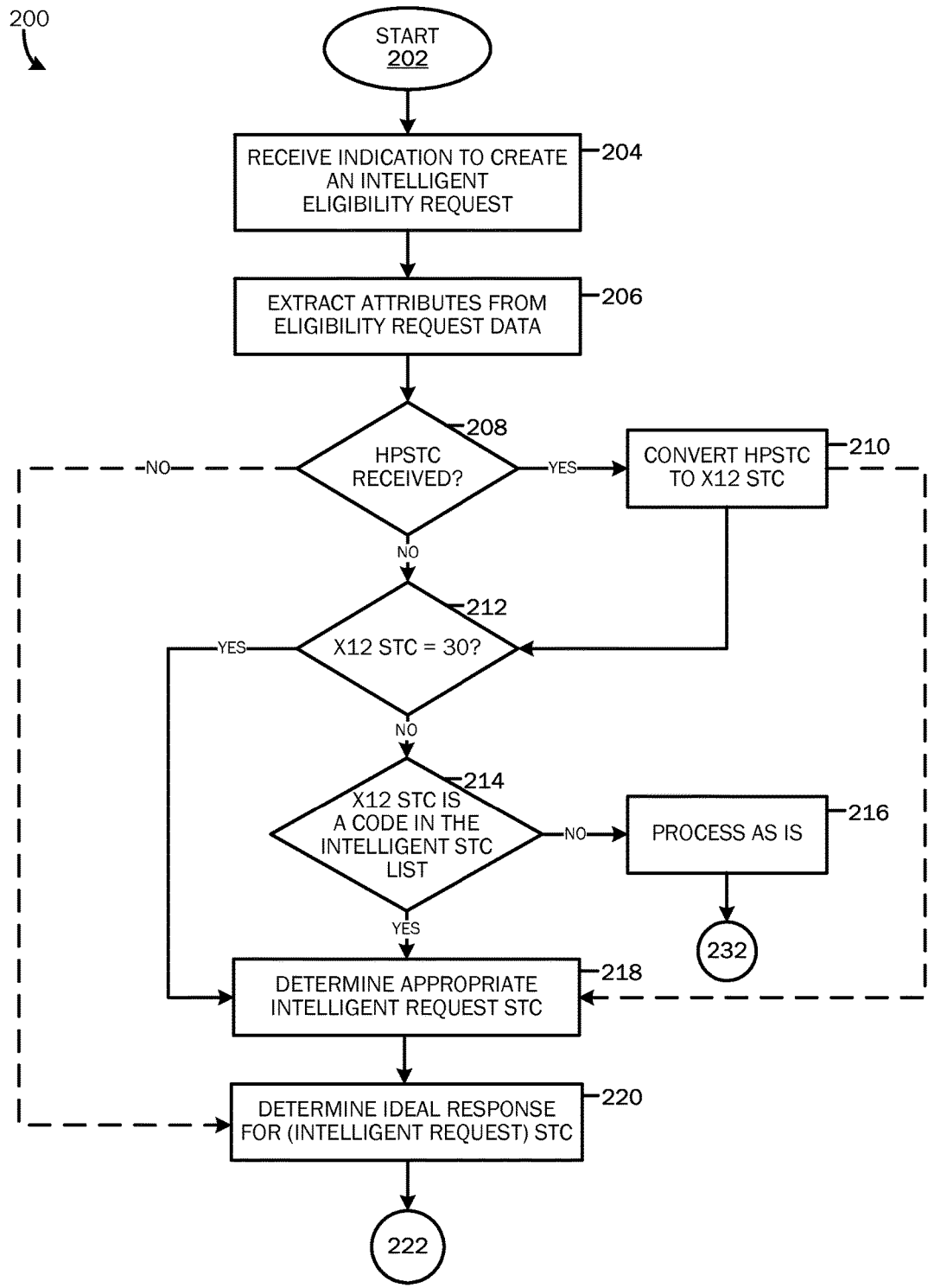
FIGS. 2A and 2B illustrate a flow chart of a method for providing an intelligent eligibility request.
Figure 2B:
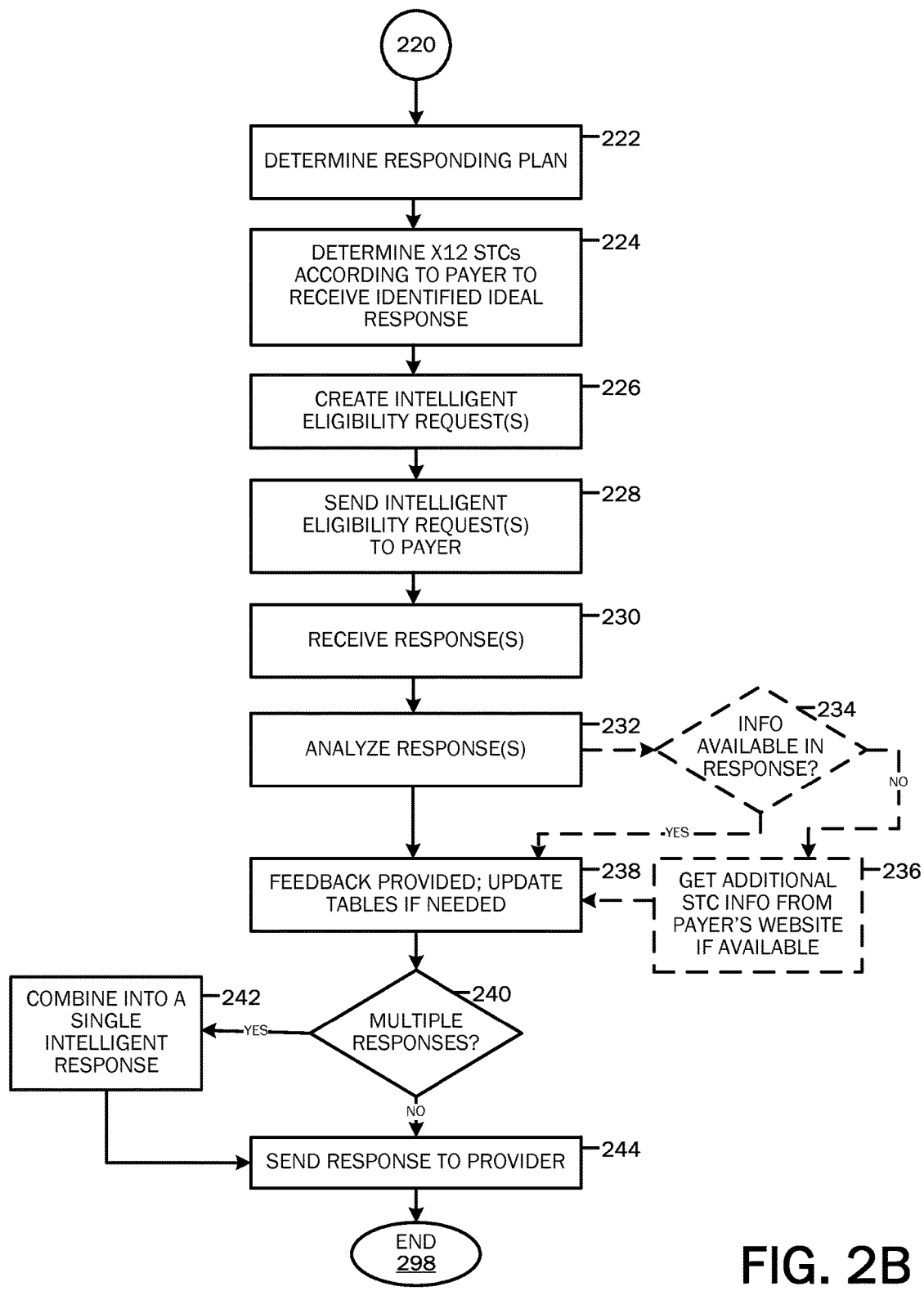

Having described a high-level system architecture 100 with which embodiments of the invention may be implemented, FIGS. 2A and 2B are a flow chart of a method for providing an intelligent eligibility request 114. The method 200 starts at OPERATION 202 and proceeds to OPERATION 204, where an indication to create an intelligent eligibility request 114 may be received. According to embodiments, the indication to create an intelligent eligibility request 114 may include receiving an eligibility request 106 (e.g., a 270 eligibility request) or receiving data that may be utilized to complete an eligibility request 106.

At OPERATION 206, various attributes from the eligibility request 106 or data may be extracted. As described above, the various attributes may include, but are not limited to, a client ID, a DLPVID, a transaction reference number, a member ID, an X12 STC or a hospital proprietary STC (HPSTC), a request source, a trading partner ID, a user ID, a department type, other HIS standard data (e.g., HL7) data (e.g., patient class, assigned patient location, admission type, admit source, patient type, etc.), other X12 data (e.g., placed of service, provider role, etc.), etc. According to an embodiment, if multiple STCs are received, a determination may be made as to whether multiple X12 STCs will be supported in the intelligent eligibility request object.

The method 200 may then proceed to DECISION OPERATION 208, where a determination may be made as to whether an HIS standard HPSTC, such as an HL7 based hospital proprietary STC, is received. If a determination is made that an attribute extracted from the received eligibility request data is an HPSTC, the method 200 may proceed to OPERATION 210, where the HPSTC may be mapped to an X12 STC according to the received client ID.

According to an embodiment and as will be described in greater detail below, the method may proceed from DECISION OPERATION 208 or OPERATION 210 to OPERATION 220 (skip OPERATIONS 212-218).

If a determination is made at DECISION OPERATION 208 that an HIS standard HPSTC is not received or after a received HPSTC is converted to an X12 STC, the method

200 may proceed to DECISION OPERATION 212, where a determination may be made as to whether an X12 STC is a code 30, which is a request for health benefit plan coverage. As is known in the art, the 5010 270/271 response 112 for a service type code 30 requires identifying up to ten high level categories of benefits if the categories are part of the plan in which the patient is active. This may be referred to as "the generic response" and returns service type codes 1 (Medical Care), 33 (Chiropractic), 35 (Dental Care), 47 (Hospital), 86 (Emergency Services), 88 (Pharmacy), 98 (Professional (Physician) Visit—Office), AL (Vision (Optometry)), MH (Mental Health), and UC (Urgent Care). These benefits may only be returned if the patient has active coverage for them.

If a determination is made that an X12 STC is not a code 30, the method 200 may proceed to DECISION OPERATION 214, where a determination may be made as to whether the X12 STC is a code in a listing of intelligent request STCs for which ideal response STCs have been identified. According to an embodiment, DECISION OPERATION 214 may comprise querying the intelligent request STC to ideal response STC mapping table described above. If the received X12 STC is not in the listing of intelligent request STCs, the received eligibility request 106 may be processed as-is and sent to a payer 108. If the received X12 STC is an intelligent request STC, the method may proceed to OPERATION 218, where the intelligent request STC may be provided as an output.

If at DECISION OPERATION 212, a determination is made that the X12 STC is a code 30, the method 200 may proceed to OPERATION 218, where other attributes may be utilized to determine an appropriate intelligent request STC. According to embodiments, depending on the provider 110 (i.e., source of the eligibility transaction), the attributes may vary, but may include some or all of: a trading partner ID, client ID, user ID, department, or other 270 attributes that may be utilized to identify a "who" and "where" associated with an eligibility request 106.

The method 200 may then proceed to OPERATION 220, where the intelligent request STC determined at OPERATION 218 may be mapped to one or more X12 STCs that represent an ideal response for the intelligent request STC. That is, a determination may be made as to what data an ideal response 112 may comprise according to the provider 110 sending the request 106 and the attributes included in the request. According to an embodiment, the intelligent request STC to ideal response STC mapping table described above may be queried to determine the one or more STCs to include in the intelligent eligibility request 114 in order to receive an ideal response (i.e., ideal response STCs).

According to another embodiment and as briefly described above, the method 200 may exclude OPERATIONS 212-218, and may proceed from DECISION OPERATION 208 or OPERATION 210 directly to OPERATION 220. That is, an eligibility request 106 or eligibility request data may be received and, instead of determining the "who" and "where" sending the request 106 (e.g., provider 110, department type, patient location, admission type, admit source, patient type, place of service, provider role, etc.), an ideal response may be determined according to the received STC(s). For example, an eligibility request 106 from a provider 110, such as a hospital, may be received. The eligibility request 106 may include a code 86 ("Emergency Services" code). At OPERATION, 220, the intelligent request STC to ideal response STC mapping table described above may be queried to determine what STCs an ideal response 112 may comprise for the 86 STC.

At OPERATION 222, a responding plan may be determined. A destination DLPVID may be determined for the payer 108 who will be actually responding to the intelligent eligibility request 114. According to an embodiment, a determination may be made if an intelligent attribute DLPVID is for a particular payer 108, for example, a payer 108 that may be part of an part of the same association of payers, where each payer 108 may respond to requests 106,114 differently (e.g., BlueCross BlueShield®). If the DLPVID attribute is for a payer 108 of an association, the member ID attribute may be analyzed to determine a home state associated with the plan, which may be used as the destination DLPVID output. According to an embodiment, the member ID attribute may be analyzed to determine a line of business associated with the plan, such as an HMO, PPO, etc., that may respond differently for each plan type.

The method 200 may then proceed to OPERATION 224, where the X12 STCs to send to the payer 108 to receive the identified ideal response X12 STCs may be determined. As described above, since each payer 108 may have different capabilities to respond to an X12 STC (e.g., some payers 108 may respond with many related STCs, while other payers 108 may respond with only the same STC as received), a determination may be made as to what may be a least number of X12 STCs to send to the payer 108 to receive the maximum number of the ideal response X12 STCs from the list of ideal X12 STCs.

According to an embodiment, the payer X12 STC response table may be queried using the destination DLPVID to locate the payer 108 associated with the eligibility request. The appropriate intelligent response type for the intelligent attribute client ID (e.g., benefit coverage, financial responsibility, etc.) may be determined. A list of payer X12 STCs may be provided as an output, the list comprising the maximum number or a percentage of the maximum number of X12 STCs that may be sent to the payer 108 without causing a timeout issue (for example, by trying to get too many of the ideal X12 STCs back from the payer 108).

At OPERATION 226, the determined X12 STCs may be included in one or more intelligent eligibility requests 114, the number of intelligent eligibility requests 114 determined depending on the payer's 108 capabilities. The method 200 may then proceed to OPERATION 228, where the one or more intelligent eligibility requests 114 may be sent to the payer 108.

At OPERATION 230, one or more eligibility responses 112 may be received. At OPERATION 232, the eligibility response(s) 112 may be analyzed. According to an embodiment, a filtering process may be performed to remove any irrelevant STCs in the event that the most efficient way to return all the needed STC codes for a given category also returns STC codes that are irrelevant to that category. For example, if the most efficient way to return CT/MRI benefits was to submit an STC of 30 to the payer (rather than sending 6 individual requests), embodiments may provide for filtering out all the benefits other than STC 62, 4, 50, 73, 9, 96 and 30.

At DECISION OPERATION 234, a determination may be made as to whether any of the requested data is not available in the eligibility response(s) 112. If there is requested data that is not included in the eligibility response(s) 112, at OPERATION 236, the payer's website may be searched for additional STC information. According to an embodiment, OPERATION 236 may be performed if the requesting provider 110 has an embellishment feature subscription.

The method 200 may proceed to OPERATION 238, where feedback may be provided and the one or more tables 120 may be updated if needed. For example, responses 112 may be monitored for new STCs returned and for expected STCs that are not returned.

At DECISION OPERATION 240, a determination may be made as to whether multiple responses 112 are received. If multiple responses 112 are received, the method 200 may proceed to OPERATION 242, where the multiple responses may be combined into a single intelligent response 112. At OPERATION 244, the single intelligent response 112 may be sent to the requesting provider 110. The method ends at OPERATION 298.

Embodiments of the invention may be implemented via local and remote computing and data storage systems. Such memory storage and processing units may be implemented in a computing device, such as computing device 300 of FIG. 3. Any suitable combination of hardware, software, or firmware may be used to implement the memory storage and processing unit. For example, the memory storage and processing unit may be implemented with computing device 300 or any other computing devices 318, in combination with computing device 300, wherein functionality may be brought together over a network in a distributed computing environment, for example, an intranet or the Internet, to perform the functions as described herein. Such systems, devices, and processors (as described herein) are examples and other systems, devices, and processors may comprise the aforementioned memory storage and processing unit, consistent with embodiments of the invention.

Figure 3:
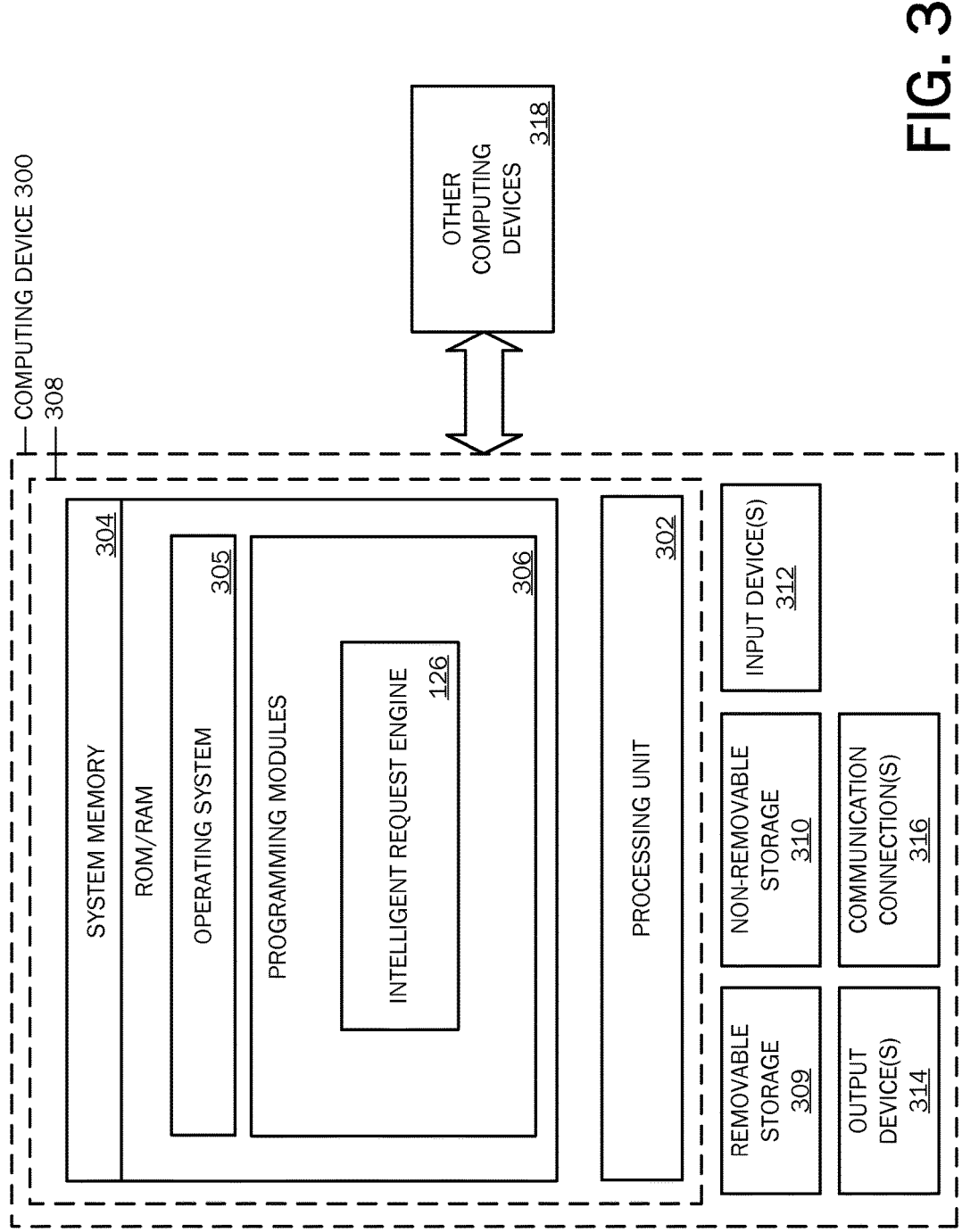
FIG. 3 is a simplified block diagram of a computing device with which embodiments of the present invention may be practiced.

With reference to FIG. 3, a system consistent with embodiments of the invention may include one or more computing devices, such as computing device 300. The computing device 300 may include at least one processing unit 302 and a system memory 304. The system memory 304 may comprise, but is not limited to, volatile (e.g. random access memory (RAM)), non-volatile (e.g. read-only memory (ROM)), flash memory, or any combination. System memory 304 may include operating system 305, one or more programming modules 306, and may include an intelligent request engine 126, wherein intelligent request engine 126 is a software application having sufficient computer-executable instructions, which when executed, performs functionalities as described herein. Operating system 305, for example, may be suitable for controlling computing device 300's operation. Furthermore, embodiments of the invention may be practiced in conjunction with a graphics library, other operating systems, or any other application program and is not limited to any particular application or system. This basic configuration is illustrated in FIG. 3 by those components within a dashed line 308. Computing device 300 may also include one or more input device(s) 312 (keyboard, mouse, pen, touch input device, etc.) and one or more output device(s) 314 (e.g., display, speakers, a printer, etc.).

Although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data and/or computer-executable instructions readable by a computing device. Computer-readable storage medium do not include communications media.

Further, the disclosed methods' stages may be modified in any manner, including by reordering stages and/or inserting or deleting stages, without departing from the invention.

The computing device 300 may also include additional data storage devices (removable and/or non-removable) such as, for example, magnetic disks, optical disks, or tape. Such additional storage is illustrated in FIG. 3 by a removable storage 309 and a non-removable storage 310. Computing device 300 may also contain a communication connection 316 that may allow device 300 to communicate with other computing devices 318, such as over a network in a distributed computing environment, for example, an intranet or the Internet. Communication connection 316 is one example of communication media.

Program modules, such as the intelligent request engine 126, may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. Accordingly, the present invention may be embodied in hardware and/or in software (including firmware, resident software, microcode, etc.). In other words, embodiments of the present invention may take the form of a computer program product on a computer-usable or computer-readable storage medium having computer-usable or computer-readable program code embodied in the medium for use by or in connection with an instruction execution system.

Embodiments of the present invention, for example, are described above with reference to block diagrams and/or operational illustrations of methods, systems, and computer program products according to embodiments of the invention. For example, FIGS. 1-3 and the described functions taking place with respect to each illustration may be considered steps in a process routine performed by one or more local or distributed computing systems. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While the specification includes examples, the invention's scope is indicated by the following claims. Furthermore, while the specification has been described in language specific to structural features and/or methodological acts, the claims are not limited to the features or acts described above. Rather, the specific features and acts described above are disclosed as example for embodiments of the invention.

It will be apparent to those skilled in the art that various modifications or variations may be made in the present invention without departing from the scope or spirit of the invention. Other embodiments of the invention will be apparent to those skilled in the art from consideration of the specification and practice of the invention disclosed herein.

All rights including copyrights in the code included herein are vested in and the property of the Applicant. The Applicant retains and reserves all rights in the code included herein, and grants permission to reproduce the material only in connection with reproduction of the granted patent and for no other purpose.

We claim:

1. A computer system comprising:
an intermediary computer system disposed between a provider computer system and a payer computer system, the intermediary computer system to:
  receive an eligibility request containing eligibility request data from the provider computer system;
  in response to receipt of the eligibility request from the provider computer system:
    create an intelligent eligibility request to send to the payer computer system that includes one or more appropriate component service type codes (STCs) and one or more appropriate explicit STCs, wherein the one or more appropriate component STCs and one or more appropriate explicit STCs are determined according to: the eligibility request data received from the provider computer system and an average response time to respond to eligibility requests according to a communication pathway associated with the payer computer system, wherein the intermediary computer system creates the intelligent eligibility request with the one or more appropriate component STCs and one or more appropriate explicit STCs to prompt the payer computer system to provide a particular eligibility response having one or more desired response STCs without experiencing a time out according to a time out value; and
    send the intelligent eligibility request as an electronic transmission to the payer computer system with the one or more appropriate component STCs and one or more appropriate explicit STCs to prompt the payer computer system to provide the particular eligibility response having the one or more desired response STCs.

2. The system of claim 1, further to:
determine the eligibility request data comprises a hospital proprietary service type code; and
convert the hospital proprietary service type code to a transaction standard format service type code.

3. The system of claim 1, further to:
determine the eligibility request data comprises a service type code 30;
identify a source of the eligibility request data via the attributes from the eligibility request data; and
determine the one or more appropriate component STCs and one or more appropriate explicit STCs to include in the intelligent eligibility request according to the identified source of the eligibility request data.

4. The system of claim 1, further to:
determine a least number of the one or more appropriate component STCs and one or more appropriate explicit STCs to include in a single eligibility request that yield a maximum number of the response data service type codes; and
insert the determined number or a percentage of the determined number of the one or more appropriate component STCs and one or more appropriate explicit STCs in one or more intelligent eligibility requests.

5. The system of claim 1, further to:
receive an eligibility response in response to the intelligent eligibility request;
analyze the eligibility response;
pursuant to a determination that multiple eligibility responses are received, combine the multiple eligibility responses into a single eligibility response; and
provide the single eligibility response to a source of the eligibility request data.

6. The system of claim 5, further to:
determine response data is missing from the eligibility response;
search for and retrieve response service type code data from a webpage of an entity providing the eligibility response; and
insert the response service type code data into the eligibility response.

7. A non-transitory computer readable medium containing computer executable instructions which, when executed by a processor:
use an intermediary computer system disposed between a provider computer system and a payer computer system, the intermediary computer system to:
  receive an eligibility request containing eligibility request data from the provider computer system;
  in response to receipt of the eligibility request from the provider computer system:
    create an intelligent eligibility request to send to the payer computer system that includes one or more appropriate component service type codes (STCs) and one or more appropriate explicit STCs, wherein the one or more appropriate component STCs and one or more appropriate explicit STCs are determined according to: the eligibility request data received from the provider computer system and an average response time for the payer computer system to respond to eligibility requests according to a communication pathway associated with the payer computer system, wherein the intermediary computer system creates the intelligent eligibility request with the one or more appropriate component STCs and one or more appropriate explicit STCs to prompt the payer computer system to provide a particular eligibility response having one or more desired response STCs without experiencing a time out according to a time out value; and
    send the intelligent eligibility request as an electronic transmission to the payer computer system with the one or more appropriate component STCs and one or more appropriate explicit STCs to prompt the payer computer system to provide the particular eligibility response having the one or more desired response STCs.

8. The non-transitory computer readable medium of claim 7, wherein the computer executable instructions which, when executed by the processor:
   determine the eligibility request data comprises a hospital proprietary service type code; and
   convert the hospital proprietary service type code to a transaction standard format service type code.

9. The non-transitory computer readable medium of claim 7, wherein the computer executable instructions which, when executed by the processor:
   determine the eligibility request data comprises a service type code 30;
   identify a source of the eligibility request data via the attributes from the eligibility request data; and
   determine the one or more appropriate component STCs and one or more appropriate explicit STCs to include in the intelligent eligibility request according to the identified source of the eligibility request data.

10. The non-transitory computer readable medium of claim 7, wherein the computer executable instructions which, when executed by the processor:
    determine a least number of the one or more appropriate component STCs and one or more appropriate explicit STCs to include in a single eligibility request that yield a maximum number of the response data service type codes; and
    insert the determined number or a percentage of the determined number of the one or more appropriate component STCs and one or more appropriate explicit STCs in one or more intelligent eligibility requests.

11. The non-transitory computer readable medium of claim 7, wherein the computer executable instructions which, when executed by the processor:
    receive an eligibility response in response to the intelligent eligibility request;
    analyze the eligibility response;
    pursuant to a determination that multiple eligibility responses are received, combine the multiple eligibility responses into a single eligibility response; and
    provide the single eligibility response to a source of the eligibility request data.

12. The non-transitory computer readable medium of claim 7, wherein the computer executable instructions which, when executed by the processor:
    determine response data is missing from the eligibility response;
    search for and retrieve response service type code data from a webpage of an entity providing the eligibility response;
    insert the response service type code data into the eligibility response; and
    provide feedback for updating response data service type codes.

13. A method comprising:
    using an intermediary computer system disposed between a provider computer system and a payer computer system to create an intelligent eligibility request, the intermediary computer system:
      receiving an eligibility request containing eligibility request data from the provider computer system;
      in response to receipt of the eligibility request from the provider computer system:
        creating the intelligent eligibility request to send to the payer computer system that includes one or more appropriate component service type codes (STCs) and one or more appropriate explicit STCs, wherein the one or more appropriate component STCs and one or more appropriate explicit STCs are determined according to: the eligibility request data received from the provider computer system and an average response time for the payer computer system to respond to eligibility requests according to a communication pathway associated with the payer computer system, wherein the intermediary computer system creates the intelligent eligibility request with the one or more appropriate component STCs and one or more appropriate explicit STCs to prompt the payer computer system to provide a particular eligibility response having one or more desired response STCs without experiencing a time out according to a time out value; and
      sending the intelligent eligibility request as an electronic transmission to the payer computer system with the one or more appropriate component STCs and one or more appropriate explicit STCs to prompt the payer computer system to provide the particular eligibility response having the one or more desired response STCs.

14. The method of claim 13, further comprising:
    determining the eligibility request data comprises a hospital proprietary service type code; and
    converting the hospital proprietary service type code to a transaction standard format service type code.

15. The method of claim 13, further comprising:
    determining the eligibility request data comprises a service type code 30;
    identifying a source of the eligibility request data via the attributes from the eligibility request data; and
    determining the one or more appropriate component STCs and one or more appropriate explicit STCs to include in the intelligent eligibility request according to the identified source of the eligibility request data.

16. The method of claim 13, further comprising:
    determining a least number of the one or more appropriate component STCs and one or more appropriate explicit STCs to include in a single eligibility request that yield a maximum number of the response data service type codes; and
    inserting the determined number or a percentage of the determined number of the one or more appropriate component STCs and one or more appropriate explicit STCs in one or more intelligent eligibility requests.

17. The method of claim 16, further comprising determining how many appropriate component STCs and appropriate explicit STCs an identified entity to provide a response can process in a single eligibility request without the payer computer system having a time out issue.

18. The method of claim 13, further comprising:
    receiving an eligibility response in response to the intelligent eligibility request;
    analyzing the eligibility response;
    pursuant to a determination that multiple eligibility responses are received, combining the multiple eligibility responses into a single eligibility response; and
    providing the single eligibility response to a source of the eligibility request data.

19. The method of claim 18, further comprising:
    determining response data is missing from the eligibility response;

searching for and retrieving response service type code data from a webpage of an entity providing the eligibility response; and inserting the response service type code data into the eligibility response.

20. The method of claim 18, further comprising providing feedback for updating response data STCs.

* * * * *